United States Patent [19]

Pinza et al.

[11] Patent Number: 4,797,496

[45] Date of Patent: Jan. 10, 1989

[54] PROCESS FOR THE PREPARATION OF PYRROLIDONE DERIVATIVES

[75] Inventors: Mario Pinza, Corsico; Ugo C. Pfeiffer, Milan, both of Italy

[73] Assignee: I.S.F. Societa Per Azioni, Milan, Italy

[21] Appl. No.: 165,340

[22] Filed: Mar. 8, 1988

Related U.S. Application Data

[63] Continuation of Ser. No. 92,250, Sep. 2, 1987, abandoned, which is a continuation of Ser. No. 705,818, Feb. 26, 1985, abandoned.

[30] Foreign Application Priority Data

Feb. 27, 1984 [IT]  Italy ................................ 19802 A/84

[51] Int. Cl.⁴ ......................................... C07D 207/12
[52] U.S. Cl. .................................... 548/544; 548/301; 560/39; 560/169
[58] Field of Search ......................................... 548/544

[56] References Cited

U.S. PATENT DOCUMENTS 4,118,396 10/1978 Pifferi et al. .................... 548/544 X
4,124,594 11/1978 Monguzzi et al. ............. 260/326.43
4,173,569 11/1979 Banfi et al. ...................... 260/326.43
4,476,308 10/1984 Aschwanden et al. ......... 548/544 X

FOREIGN PATENT DOCUMENTS 1059137 7/1979 Canada .
57-183756 11/1982 Japan .................................. 548/544

OTHER PUBLICATIONS

Noller, Chemistry of Organic Compounds, 3rd Ed. (1965), pp. 813–814.
Pifferi et al., Il Farmaco (Ed. Sc.) 32: 602–613 (1977).

*Primary Examiner*—Joseph Paul Brust
*Attorney, Agent, or Firm*—Nancy S. Mayer; Janice E. Williams; Alan D. Lourie

[57] ABSTRACT

Process for preparing pyrrolidinone derivatives of (1)

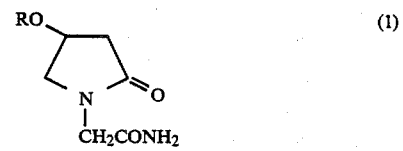

in which R is hydrogen, alkyl or acyl characterized in that a compound of (2)

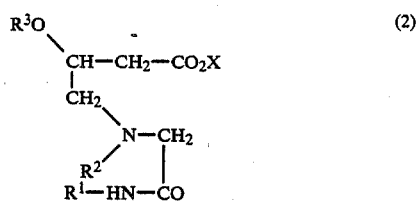

wherein $R^1$ is hydrogen and $R^2$ is benzyl or substituted benzyl, or $R^1$ and $R^2$ can together form a group

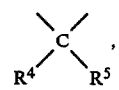

where $R^4$ and $R^5$ are independently hydrogen, alkyl, phenyl or optionally substituted aryl or together are 1,4-butylene or 1,5-pentylene; $R^3$ is hydrogen or straight or branched alkyl of 1 to 4 carbon atoms; and X is alkyl subjected to N-deprotection and the deprotected intermediate is cyclized intramolecularly.

The deprotected intermediates can be isolated as acid-addition salts.

24 Claims, No Drawings

PROCESS FOR THE PREPARATION OF PYRROLIDONE DERIVATIVES

This is a continuation of application Ser. No. 092,250, filed Sept. 2, 1987, which is a continuation of Ser. No. 705,818, filed Feb. 26, 1985, both now abandoned.

The present invention concerns a process for preparing pyrrolidinone derivatives, more specifically 2-oxo-1-pyrrolidineacetamide derivatives, which may also be called 1-carbamoylmethyl-2-pyrrolidinone derivatives.

It is known that 4-substituted derivatives of 2-oxo-1-pyrrolidineacetamide are valued psychotropic agents that, in animals and man, restore cognitive function that has been damaged as a result of various pathologies. These drugs are described for example in Pharm. Res. Commun. 16, 67 (1984) by Banfi et al, or in Drug Development Res. 2, 447 (1982) by T M Itil et al.

Known processes for preparing the above pyrrolidinone derivatives which are described in U.S. Pat. Nos. 4,124,594 and 4,173,569 start from gamma-amino-beta-hydroxybutyric acid, and involve several steps such as protection with a silylating agent, alkylation, cyclisation and final aminolysis to give the carbamoylmethyl group attached to the heterocyclic nitrogen atom. These kinds of known processes involves the use of particular anhydrous solvents and of bases or of acid-accepting compounds, which require special equipment and precautions in order to maintain an anhydrous environment.

The main aim of the present invention is to provide a process for the preparation of 2-oxo-1-pyrrolidineacetamide which does not require the use of anhydrous conditions, nor, therefore, the equipment and precautions that would otherwise be necessary. A further aim of the present invention is to provide a process that makes use of cheap and readily available starting materials. Another aim of the present invention is to provide a process that permits the desired 2-oxo-1-pyrrolidineacetamide derivatives to be obtained with good selectivity.

According to the present invention there is provided a process for preparing a pyrrolidinone derivative of structure (1)

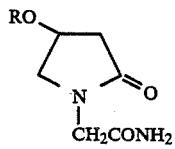

in which R is hydrogen, straight or branched alkyl of 1 to 4 carbon atoms, or acyl containing 1 to 10 carbon atoms, characterised in that a compound of structure (2)

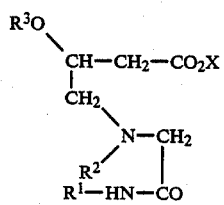

wherein $R^1$ is hydrogen and $R^2$ is benzyl or substituted benzyl, or $R^1$ and $R^2$ can together form a group

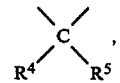

where $R^4$ and $R^5$ are independently hydrogen, alkyl containing 1 to 4 carbon atoms, optionally substituted aryl or together are 1,4-butylene or 1,5-pentylene $(-(CH_2)_5-)$;

$R^3$ is hydrogen or straight or branched alkyl of 1 to 4 carbon atoms; and

X is straight or branched alkyl containing 1 to 10 carbon atoms;

is subjected to N-deprotection to give a compound of structure (3)

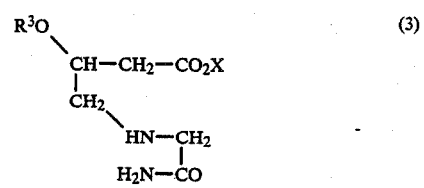

which is cyclized intramolecularly; and optionally when $R^3$ is hydrogen the product is converted into a compound in which R is acyl or alkyl.

In compound (1), "acyl" in the definition of R is, suitably, alkanoyl; in compound (2) "substituted benzyl" in the definition of $R^2$ is suitably α-methylbenzyl or p-methoxy benzyl and "optionally substituted aryl" in the definition of $R^4$ and $R^5$ is suitably phenyl.

In compound (2) preferably $R^1$ and $R^2$ together form a 2-methyl-propan-1,1-diyl group ($<CHCH(CH_3)_2$).

In compound (2) preferably $R^3$ is hydrogen.

When $R^2$ is benzyl or substituted benzyl the compound of structure (2) can be deprotected via catalytic hydrogenation using for instance a 5% Pd/C catalyst at temperatures between 0° and 40° C. and at pressures between ambient and 10 Torr. The reaction is performed in a suitable solvent, e.g. alcohol, an aliphatic or aromatic hydrocarbon, water, or mixture of these. Alternatively debenzylation can be achieved by treatment with a mixture of formic acid and methanol. and Pd/C The subsequent cyclisation takes place at 0° to 120° C., preferably 60° to 80° C., with or without solvent. The solvent, if used, is selected from those mentioned above for the debenzylation, or is acetonitrile.

When $R^1$ and $R^2$ together form a group

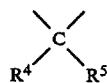

deprotection and intramolecular cyclisation can be effected by heating with water at temperatures between 90° and 160° C., preferably between 100° and 130° C. It is convenient to use water or mixtures of solvents and water. Preferably the solvent is a 95% mixture of an organic solvent with water (5%). As organic co-solvents may be used dimethylformamide (DMF), dimethylsulphoxide (DMSO), dimethylacetamide (DMA), acetonitrile and alcohols such as ethanol, etc. Preferably the reaction is carried out in the presence of a carboxylic acid, e.g. acetic acid or benzoic acid. Although catalytic quantities of carboxylic acids are effective preferably about one molar equivalent of a carboxylic acid is used.

The compound of structure (1) in which R is hydrogen is oxiracetam and is a particularly useful product of this invention.

The compounds of structure (1) in which R is hydrogen can be converted into a compound in which R is acyl or alkyl by reaction with an acyl halide (preferably a chloride) or acid anhydride using conventional procedures, or by using an alkyl halide (preferably a bromide or iodide) or sulphate using conventional procedures.

The compounds prepared by the process of the present invention have a centre of asymmetry at the carbon atom in the 4-position, where the $-OR$ substituent is attached, hence it is possible to obtain them as separate enantiomers or as a racemic mixture thereof.

If desired the deprotected intermediates of structure (3) may be isolated, preferably in the form of a salt with an acid selected from organic or inorganic acids such as hydrochloric, hydrobromic, sulphuric, p-toluenesulphonic, acetic, oxalic, maleic, malic acids etc. A preferred intermediate of structure (2) is that wherein $R^3$ is hydrogen and $R^1$ and $R^2$ together form a 2-methyl-propan-1,1-diyl group.

The intermediates of structure (2) and (3) are novel and form an important aspect of this invention.

The intermediates of structure (2) can be prepared by reacting

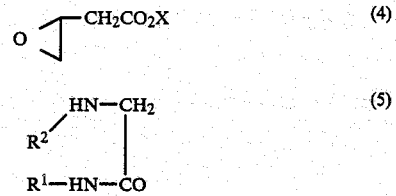

an alkyl 3,4-epoxybutanoate of the structure (4) where X is alkyl of 1–10 carbon atoms, with a glycineamide derivative of structure (5) (in which $R^1$ and $R^2$ are as defined in structure (2)) to form a compound of structure (2) in which $R^3$ is hydrogen; and optionally reacting the product with an alkyl halide (preferably a bromide or iodide), dialkyl sulphate, acyl halide (preferably a chloride) or acid anhydride to form a compound of structure (2) in which $R^3$ is other than hydrogen.

The condensation reaction between (4) and (5) may take place without the use of solvents or in the presence of organic solvents, water or mixtures of these in proportions of from 1:5 to 20:1, preferable from 1:1 to 1:3 or organic solvent and water. As organic solvent may be used a wide variety of inert solvents e.g. acetonitrile, alcohols such as isopropanol, acetone etc.

The condensation is performed at a temperature of 20° to 120° C., preferably 70°–100° C. In the condensation phase the two reagents may be used in stoichiometric proportions, or an excess of one of them may be used, preferably a ratio of from 1:1 to 1:1.1 of the amine derivative (5) and the epoxyester (4).

The intermediate of structure (2) in which $R^3$ is hydrogen that results from the condensation may be isolated and purified, or may be converted at once into compound I, by deprotection and cyclisation. These reactions may be carried out in the same mixture as the condensation reaction, in the absence of solvent, with the same solvent, or by replacing the initial solvent with one or more high-boiling solvents.

The alkyl 3,4-epoxybutanoates (4) can be prepared by known methods described in the literature, for instance from alkyl 3,4-butenoates by epoxidation with peroxide compounds such as organic and inorganic peracids, hydrogen peroxide etc, (e.g. by the general procedure of C. Venturello et al. *J. Org. Chem.* 48 3831 (1983) or by dehydrohalogenation of 3-halo-4-hydroxybutyrates (cf R Rambaud and S Ducher, Bull. Soc. Chim. Fr., 466 (1966)).

The imidazolidinones of structure (5) in which $R^1$ and $R^2$ together form a group

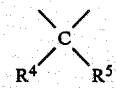

may be prepared from glycineamide and suitable carbonyl compounds, or from alkyl alkylidenaminoacetates and ammonia, by methods described in the literature, e.g. A. C. Davis and A. L. Levy, J. Chem. Soc., 3479 (1951); P. G. Wiering and H. Steinberg, Rec. Trav. Chim. Pays-Bas 111, 284 (1971).

The invention is illustrated by the following Preparations and Examples:

PREPARATION 1

2-Methylpropyl-3,4-epoxybutanoate

Sodium tungstate dihydrate (0.852 g, 2.5 mmol), 85% phosphoric acid (0.850 ml, 5 mmol) 36.3% hydrogen peroxide (5.6 ml, 60 mmol) were dissolved in 20 ml of water and the pH was adjusted to 1.6 by 10% sulphuric acid. The solution was heated to 70° C., and under vigorous stirring a solution of 2-methylpropyl 3-butenoate (7.1 g, 50 mmol), trimethylcaprylammonium chloride (0.41 g) in 1,2-dichloroethane (15 ml) was added. After 6 hours the mixture was cooled, then the layers were separated. The aqueous phase was washed with 30 ml of dichloroethane. Organic layers were collected, washed with 2×40 ml of saturated solution or sodium sulphite, dried and distilled. The title compound was obtained as a colourless oil, b.p. 104°–108° 30 mmHg.

PREPARATION 2

(a) A stream of hydrogen was bubbled into a solution of 2-methylpropyl-4-[N-(carbamoylmethyl)benzylamino]-3-hydroxybutanoate (1 g) in ethanol (30 ml) containing Pd/C 5% (100 mg) for 1 hr. The catalyst was filtered and oxalic acid (0.28 g) was added. The resulting solution was chilled overnight and the precipitate was collected to give 200 mg of 2-methylpropyl 4-(carbamoylmethylamino)-3-hydroxybutanoate oxalate, m.p. 145° C. dec.

(b) In the same way, from 3 g of 2-methylpropyl 4-[N-(carbamoylmethyl)benzylamino]-3-hydroxybutanoate (3 g) and maleic acid (2.16 g) 210 mg of 2-methylpropyl-4-(carbamoylmethylamino)-3-hydroxybutanoate maleate (m.p. 109° C. dec.) were obtained.

EXAMPLE 1

1.3 g of 1,4-diazaspiro[4,5]decan-2-one ((5); $R_4+R_5=-(CH_2)_5-$) (8.4 mmoles) are heated and stirred with magnetic stirring, with 1.5 g 2-methylpropyl 3,4-epoxybutanoate ((4), X=isobutyl) (9.5 mmoles) up to 110° (external temperature) for 24 h. The mixture is cooled, and the dark mass obtained is washed with 10 ml boiling ethyl acetate. This is decanted, and the solid obtained is crystallised from methanol to give oxiracetam as a crystalline white powder, m.p. 167°–70° C.

EXAMPLE 2

1 g of 2,2-dimethyl-4-imidazolidinone ((5); $R_4=R_5=CH_3$) (8.76 mmoles) is dissolved in 5 ml acetonitrile. 1 g 2-methylpropyl 3,4-epoxybutanoate ((4); X=isobutyl) (6.32 mmoles) is added and the mixture is boiled for 30 h with stirring. The mixture is cooled, the solvent is decanted off, the resulting dark solid mass is taken up in ethanol, and the solid oxiracetam obtained is filtered off, m.p. 167°–70° C.

EXAMPLE 3

0.650 g 2,2-dimethyl-4-imidazolidinone ((5); $R_4=R_5=CH_3$) (5.7 mmoles) is dissolved in 5 ml isopropanol. 1 g 2-methylpropyl 3,4-epoxybutanoate ((4); X=isobutyl) (6.32 mmoles) is added. The mixture is boiled for 9 h. A further 1 g of epoxyester is added and boiling is continued for a further 9 h. After cooling, the solvent is decanted and the dark mass obtained is taken up in ethanol. The solid obtained is filtered, to give oxiracetam, m.p. 167°–70° C.

EXAMPLE 4

1 g of 2,2-dimethyl-4-imidazolidinone ((5); $R_4=R_5=CH_3$) (8.76 mmoles) are heated at 165° C. (external temperature) for 1 h 30 min with 2 g 2-methylpropyl 3,4-epoxybutanoate ((4); X=isobutyl) (12.64 mmoles). 0.17 ml of water and 5 ml ethanol are added, and boiling is continued for a further 2 h. The mixture is cooled and filtered. Oxiracetam is obtained as a white crystalline powder, m.p. 167°–70° C.

EXAMPLE 5

1 g of 2,2-dimethyl-4-imidazolidinone ((5); $R_4=R_5=CH_3$) (8.70 mmoles) is dissolved in 1 ml water. 1.5 g 2-methylpropyl 3,4-epoxybutanoate ((4); X=isobutyl) (9.48 mmoles) are added and the mixture is heated at 50° for 11 h with stirring by a magnetic stirrer. Heating is then continued at the boiling point for a further 11 h. The mixture is cooled, 10 ml acetone is added, stirring is performed for 30 min and the mixture is filtered. The product obtained is crystallised from methanol to give oxiractam of m.p. 167°–70° C. as a white crystalline powder.

EXAMPLE 6

0.5 g 2,2-dimethyl-4-imidazolidinone ((5); $R_4=R_5=CH_3$) (4.38 mmoles) are heated at 115° C. (external temperature) for 12 h with stirring by a magnetic stirrer, with 0.57 g ethyl 3,4-epoxybutanoate ((4); $X=C_2H_5$) (4.38 mmoles). The mixture is cooled, taken up with methanol and filtered. Oxiracetam is obtained, m.p. 167°–70° C.

EXAMPLE 7

1 g 2,2-dimethyl-4-imidazolidinone ((4); $R_4=R_5=CH_3$) (8.76 mmoles) is dissolved in 1 ml water. 2 g 2-methylpropyl 3,4-epoxybutanoate is added and stirring is continued at ambient temperature for 10 days. The oil obtained is chromatographed on silica, eluting with 1:1 acetone/methanol. The main fraction is collected, dehydrated using $MgSO_4$, and evaporated. An oil is obtained, which solidifies on rubbing, is taken up in hexane and filtered. 1.8 g 2-methylpropyl 2,2-dimethyl-4-oxo-1-imidazolidine-β-hydroxybutyrate is obtained ((2); $R_3=H$, $R_4=R_5=CH_3$, X=isobutyl), m.p. 76°–8° C., a white solid (75.5%). This compound is dissolved in 3 ml acetonitrile and 1 ml water, and boiled for 72 h. After evaporating, the product is taken up with ethanol and filtered, oxiracetam is obtained as a white crystalline powder, m.p. 167°–70° C.

EXAMPLE 8

6.52 g 2-(1-methylethyl)-4-imidazolidinone hydrochloride ((5); $R_4=H$, $R_5$=isopropyl) (0.04 moles) are dissolved in 40 ml water and treated with 2.8 g potassium carbonate (0.02 mole). 7 g 2-methylpropyl 3,4-epoxybutanoate are added ((4); X=isobutyl) (0.044 mole) and 25 ml acetone. The mixture is heated at 60° C. for 48 h with stirring. The mixture is reduced to a small volume, the solid is filtered and washed with ether. 3.5 g of a white solid, m.p. 135°–40° C. is obtained. The liquor from which this solid was separated is evaporated to dryness and chromatographed on silica, eluting with 8:2 ethylacetate/methanol. The main fractions are collected and evaporated to give a further 2.9 g compound of m.p. 135°–40° C., giving a total of 6.4 g 2-methylpropyl 2-(1-methylethyl)-4-oxo-1-imidazolidine-β-hydroxybutanoate ((2); $R_3=R_4=H$, $R_5$=isopropyl, X=isobutyl). 1 g of this compound (3.5 mmoles) is heated to boiling for 8 h in 6 ml dimethyl sulfoxide+2 ml water. After evaporation, the residue is taken up with acetone, filtered, dried in vacuo and crystallised from methanol. 0.32 g Oxiracetam is obtained as a white crystalline powder, m.p. 167°–70° C. (yield 57.8%).

EXAMPLE 9

5.8 g of 2-(1-methylethyl)-4-imidazolidinone hydrochloride ((5); $R_4=H$, $R_5$=isopropyl) (0.035 moles) are shaken in 10 ml water and treated with 2.4 g potassium carbonate (0.0174 moles). 4.5 g ethyl 3,4-epoxybutanoate and 6 ml acetone are added, and stirring is maintained for 45 h at 70° C. After evaporation, the residue is chromatographed on silica, eluting with 8:2 ethyl acetate/methanol. The main fractions are collected and evaporated. The oil that remains is taken up with ethyl acetate. After being left to stand overnight the white compound obtained is filtered: 1.3 g ethyl 2-(1-methylethyl)-4-oxo-1-imidazolidine-β-hydroxybutanoate m.p. 118°–122° C. 0.95 g of this compound (3.7 mmoles) are heated to boiling for 15 h in 4 ml DMF and 1 ml water. After evaporation in vacuo, the residue is taken up with methanol, and the solution is filtered. 0.37 g oxiracetam is obtained as a white crystalline powder, m.p. 167°–70° C. (63.2%).

EXAMPLE 10

19 g 2-(1-Methylethyl)imidazolidinone ((5); $R_4=H$, $R_5$=isopropyl) (0.15 moles) are dissolved in 100 ml water and 150 ml acetone. 2-Methylpropyl-3,4-epoxybutanoate (0.15 moles) are added and the mixture is heated and stirred for 48 h at 70° C. The acetone is evaporated in vacuo and 100 ml DMF are added, followed by boiling for 21 h. The mixture is reduced to a small volume in vacuo, the residue is taken up with 40 ml water and washed with 2×40 ml methylene chloride. The aqueous phase is evaporated to dryness and redissolved in 15 ml methanol. This is left to stand for 3 h at 0° C., filtered and dried to give oxiracetam as a white crystalline powder, m.p. 167°–70° C.

EXAMPLE 11

12 g 2-(1-methylethyl)-4-imidazolidinone hydrochloride ((5); $R_4$=H, $R_5$=isopropyl) (0.073 moles) are shaken with 20 ml water and treated with 5 g potassium carbonate (0.036 moles). 8.5 g methyl 3,4-epoxybutanoate (0.073 moles) and 12 ml acetone are added. The mixture is stirred for 45 h at 70° C. After evaporating, the residue is chromatographed on silica, eluting with 8:2 ethyl acetate/methanol. The main fractions are combined and evaporated. 2.5 g of methyl 2-(1-methylethyl)-4-oxoimidazolidine-β-hydroxybutanoate, m.p. 109°–122° C., are obtained as a white powder (14.4%). 2.0 g of this compound (0.0082 mole) are heated to boiling for 15 h with 8.8 ml DMF and 2.2 ml water. After evaporation in vacuo, the residue is taken up with methanol, and filtered. 0.74 g oxiracetam is obtained as a white crystalline powder, m.p. 167°–70° C. (57.4%).

EXAMPLE 12

A mixture of 0.7 g 2-phenylimidazolidine-4-one and 1 g 2-methylpropyl 3,4-epoxybutanoate are heated for 12 h at 70° (external temperature) in 2 ml water and 2 ml acetone. After evaporating, the residue is taken up with ether and the white solid obtained is filtered, and recrystallised from ethyl/acetate, 2-Methylpropyl-2-phenyl-4-oxoimidazolidine-β-hydroxybutanoate is obtained as a white powder, m.p. 126°–128° C.

EXAMPLE 13

A solution of 0.65 g 2-methylpropyl 2-phenyl-4-oxoimidazolidine-β-hydroxybutanoate in 1.5 ml dimethyl sulfoxide and 0.5 ml water is heated at reflux for 16 h. After evaporating, the residue is chromatographed on silica, eluting with 7:3 ethyl acetate/methanol. Oxiracetam is obtained as a white powder, m.p. 167°–70° C.

EXAMPLE 14

A. 2-Methylpropyl 4-[N-(carbamoylmethyl)benzylamino]-β-hydroxybutanoate ((2); $R_2$=CH$_2$C$_6$H$_5$, $R_3$=H, X=isopropyl).

A mixture of benzylaminoacetamide ((5) $R_1$=H, $R_2$=CH$_2$C$_6$H$_5$) (1.64 g) and 2-methylpropyl 3,4-epoxybutanoate (1.58 g) are heated for many hours at 30° C. with magnetic stirring. The reaction mixture is taken up with ligroin and the resulting solid is filtered. Recrystallisation is from ether/ligroin. 2.7 g of title compound m.p. 99°–100° C. are obtained.

B. 4-Hydroxy-2-oxo-1-pyrrolidineacetamide (oxiracetam).

A solution of compound A (1 g) in 25 ml ethanol is hydrogenated at ambient temperature and pressure in the presence of 100 mg 5% Pd/C. The catalyst is filtered off and the solvent evaporated to give 0.72 g 2-methylpropyl 4-(carbamoylmethylamino)-3-hydroxybutanoate. This compound is dissolved in situ in 10 ml acetonitrile and heated at reflux for 8 h. After evaporation of the solvent, the residue is crystallised from ethanol. Oxiracetam is obtained as a white crystalline powder of m.p. 167°–70° C.

EXAMPLE 15

1-Carbamoylmethyl-4-acetoxy-2-pyrrolidone

A mixture of 5.33 g oxiracetam and 44.3 ml acetyl chloride is heated at reflux for 15 min. After cooling, the solvent is evaporated in vacuo and the oil remaining is taken up in a little aqueous sodium bicarbonate, and solid sodium bicarbonate is added with stirring until neutrality is achieved. Most of the water present is removed by treating with methyl isobutyl ketone in vacuo, the residue is taken up with methylene chloride, dried with sodium sulphate and evaporated in vacuo. The oil remaining is triturated in isopropyl alcohol/diethyl ether and recrystallised from 20:80 isopropyl alcohol/isopropyl ether to give 1-carbamoylmethyl-4-acetoxy-2-pyrrolidone which when purified by chromatography melts at 84°–86° C.

EXAMPLE 16

4-Hydroxy-2-oxo-1-pyrrolidineacetamide (oxiracetam)

A solution of 2-methylpropyl 2-(1-methylethyl)-4-oxoimidazolidine-β-hydroxybutanoate (15 g, 52.4 mmol), benzoic acid (6.4 g, 52.4 mmol) and water (3.75 ml, 208 mmol) in n-pentanol (90 ml) was refluxed under nitrogen for 6 hr. After cooling the mixture was extracted twice with water (35 ml). The aqueous extracts were evaporated to dryness and the residue was crystallized from methanol to give 5.15 g (62.1%) of the title compound, m.p. 167°–70° C.

The description above illustrates how the process of the invention achieves the stated aims, permitting the use as starting material an easily and cheaply available glycinamide derivative, and allowing the use of aqueous solvents without the need to ensure anhydrous conditions.

The process can be worked with good selectivity for the desired compound and little formation of by-products, thanks to the use of the starting amine derivatised as a secondary amine.

What is claimed is:

1. A process for preparing a pyrrolidinone derivative of structure (1)

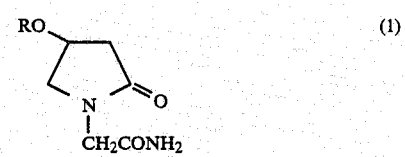

in which R is hydrogen, comprising:

(a) N-deprotecting a compound of structure (2)

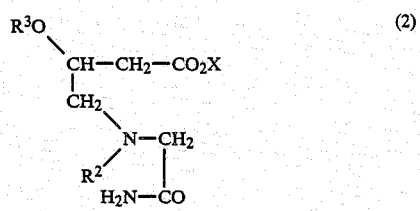

wherein $R^2$ is benzyl, α-methylbenzyl or p-methoxybenzyl;

$R^3$ is hydrogen, and X is straight or branched alkyl containing 1 to 10 carbon atoms;

to give a compound of structure (3)

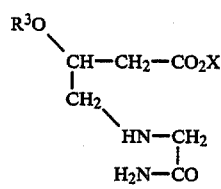

wherein X and R³ are as defined above; and
(b) cyclizing the compound of structure (3) intramolecularly by heating at 0° to 120° C.

2. A process for preparing a pyrrolidinone derivative of structure (1)

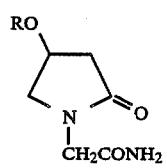

in which R is alkanoyl containing 1 to 10 carbon atoms, comprising:
(a) N-deprotecting a compound of structure (2)

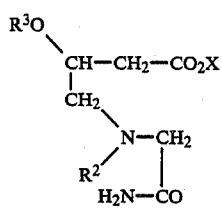

wherein
R² is benzyl, α-methylbenzyl or p-methoxybenzyl;
R³ is hydrogen; and X is straight or branched alkyl containing 1 to 10 carbon atoms;
to give a compound of structure (3)

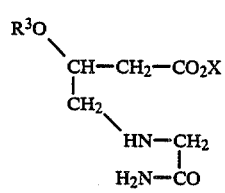

wherein X and R³ are as defined above;
(b) cyclizing the compound of structure (3) intramolecularly by heating at 0° to 120° C.; and
(c) reacting the cyclized compound with an acyl halide or acid anhydride in which acyl is an alkanoyl containing 1 to 10 carbon atoms to yield a compound of structure (1).

3. A process for preparing a pyrrolidnone derivative of structure (1)

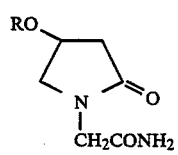

in which R is straight or branched alkyl of 1 to 4 carbon atoms comprising:
(a) N-deprotecting a compound of structure (2)

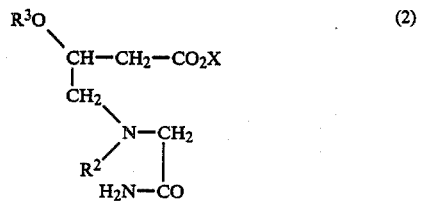

wherein
R² is benzyl, α-methylbenzyl or p-methoxybenzyl;
R³ is hydrogen; and X is straight or branched alkyl containing 1 to 10 carbon atoms;
to give a compound of structure (3)

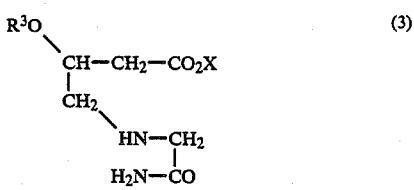

wherein X and R³ are as defined above;
(b) cyclizing the compound of structure (3) intramolecularly by heating at 0° to 120° C.; and
(c) reacting the cyclized compound with an alkyl halide or sulfate in which the alkyl contains 1 to 4 carbon atoms to yield a compound of structure (1).

4. A process for preparing a pyrrolidinone derivative of structure (1)

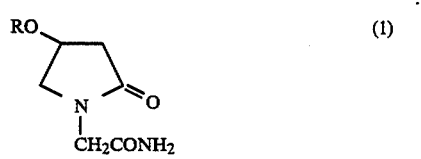

in which R is straight or branched alkyl of 1 to 4 carbon atoms comprising:
(a) N-deprotecting a compound of structure (2)

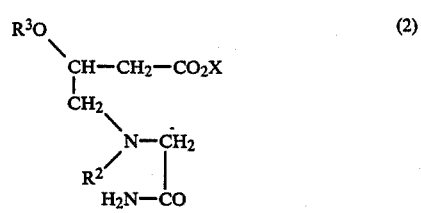

wherein
R² is benzyl, α-methylbenzyl or p-methoxybenzyl;
R³ is straight or branched alkyl of 1 to 4 carbon atoms; and X is straight or branched alkyl containing 1 to 10 carbon atoms to give a compound of structure (3)

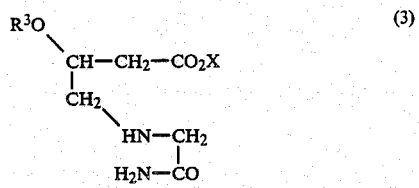

wherein X and $R^3$ are as defined above; and
(b) cyclizing said compound of structure (3) intramolecularly by heating at 0° to 120° C.

5. The process of claim 1, 2, 3 or 4 wherein the compound of structure (2) is N-deprotected by catalytic hydrogenation.

6. The process of claim 1, 2, 3 or 4 wherein the compound of structure (2) is N-deprotected by treatment with a mixture of formic acid and methanol and palladium-on-charcoal.

7. A process for preparing a pyrrolidinone derivative of structure (1)

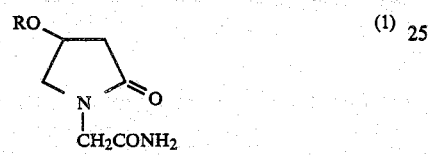

in which R is hydrogen which comprises:
(a) N-deprotecting and cyclizing intramolecularly by heating at 90° to 160° C. a compound of structure (2A)

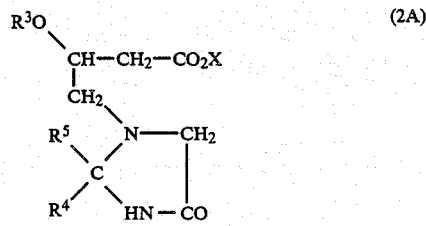

wherein
$R^4$ and $R^5$ are independently hydrogen, alkyl containing 1 to 4 carbon atoms, phenyl, or $R^4$ and $R^5$ together are 1,4-butylene or 1,5-pentylene;
$R^3$ is hydrogen; and X is straight or branched alkyl of 1 to 10 carbon atoms;
to give a compound of structure (1).

8. A process for preparing a pyrrolidinone derivative of structure (1)

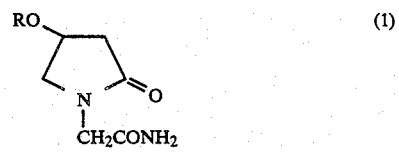

in which R is alkanoyl containing 1 to 10 carbon atoms, which comprises:
(a) N-deprotecting and cyclizing intramolecularly by heating at 90° to 160° C. the compound of structure (2A)

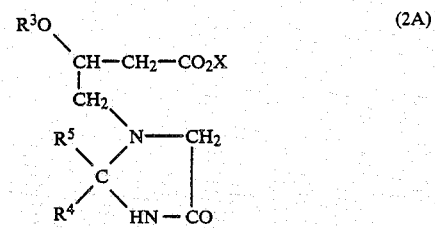

wherein
$R^4$ and $R^5$ are independently hydrogen, alkyl containing 1 to 4 carbon atoms, phenyl, or $R^4$ and $R^5$ together are 1,4-butylene or 1,5-pentylene;
$R^3$ is hydrogen; and X is straight or branched alkyl of 1 to 10 carbon atoms; and
(b) reacting the cyclized compound, with an acyl halide or acid anhydride in which acyl is alkanoyl containing 1 to 10 carbon atoms to give a compound (1).

9. A process for preparing a pyrrolidinone derivative of structure (1)

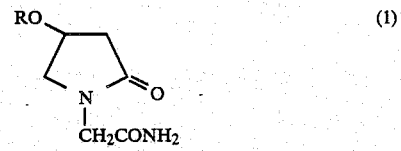

in which R is straight or branched alkyl of 1 to 4 carbon atoms, which comprises:
(a) N-deprotecting and cyclizing intramolecularly by heating at 90° to 160° C. the compound of structure (2A);

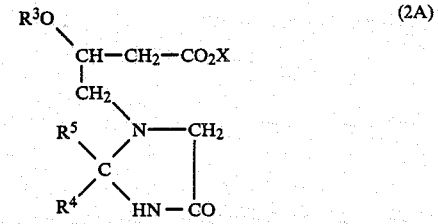

wherein
$R^4$ and $R^5$ are independently hydrogen, alkyl containing 1 to 4 carbon atoms, phenyl, or $R^4$ and $R^5$ together are 1,4-butylene or 1,5-pentylene;
$R^3$ is hydrogen; and X is straight or branched alkyl of 1 to 10 carbon atoms; and
(b) reacting the cyclized compound, with an alkyl halide or sulfate in which alkyl is of 1 to 4 carbon atoms to give a compound (1).

10. A process for preparing a pyrrolidinone derivative of structure (1)

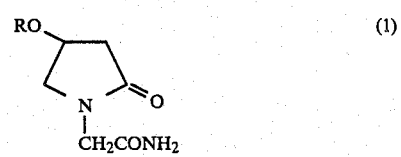

in which R is straight or branched alkyl of 1 to 4 carbon atoms, which comprises:

(a) N-deprotecting and cyclizing intramolecularly by heating at 90° to 160° C. the compound of structure (2A)

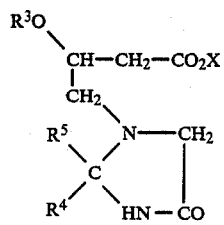
(2A)

wherein
$R^4$ and $R^5$ are independently hydrogen, alkyl containing 1 to 4 carbon atoms, phenyl, or $R^4$ and $R^5$ together are 1,4-butylene or 1,5-pentylene;
$R^3$ is a straight or branched alkyl of 1 to 4 carbon atoms; and X is straight or branched alkyl of 1 to 10 carbon atoms.

11. A process according to claim 7, 8, 9, or 10 in which the N-deprotection is effected in the presence of acetic or benzoic acid.

12. A process according to claim 7, 8, 9 or 10 in which in the compound of structure (2A) $R^4$ is hydrogen, $R^5$ is an isopropyl group and $R^3$ is hydrogen.

13. A process for preparing a pyrrolidinone derivative of structure (1)

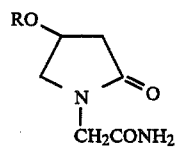
(1)

in which R is hydrogen, comprising:
(a) reacting an alkyl 3,4-epoxybutanoate of structure (4)

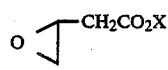
(4)

wherein X is alkyl of 1 to 10 carbon atoms with a glycinamide derivative of structure (5)

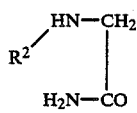
(5)

wherein $R^2$ is benzyl, α-methylbenzyl or p-methoxybenzyl to give a compound a structure (2)

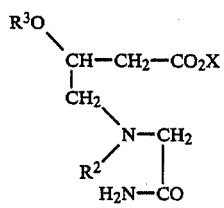
(2)

wherein X and $R_2$ are as defined above, and $R^3$ is R as defined above;

(b) N-deprotecting the compound of structure (2) to give a compound of structure (3)

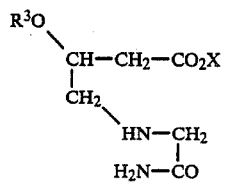
(3)

wherein X and $R^3$ are as defined above;
(c) cyclizing the compound of structure (2) intramolecularly by heating at 0° to 120° C.

14. A process for preparing a pyrrolidinone derivative of structure (1)

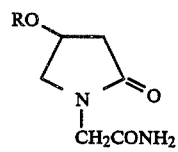
(1)

in which R is alkanoyl containing 1 to 10 carbon atoms, comprising:
(a) reacting an alkyl 3,4-epoxybutanoate of structure (4)

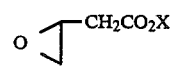
(4)

wherein X is alkyl of 1 to 10 carbon atoms with a glycinamide derivative of structure (5)

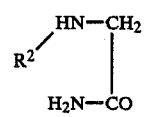
(5)

wherein $R^2$ is benzyl, α-methylbenzyl or p-methoxybenzyl to give a compound of structure (2)

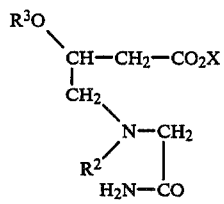
(2)

wherein X and $R_2$ are as defined above, and $R^3$ is hydrogen;
(b) N-deprotecting the compound of structure (2) to give a compound of structure (3)

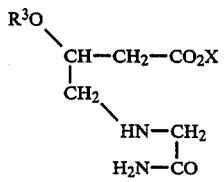
(3)

wherein X and $R^3$ are as defined above (c) cyclizing the compound of structure (3) intramolecularly by heating at 0° to 120° C.; and
(d) reacting the cyclized compound with an acyl halide or acid anhydride in which acyl is alkanoyl containing 1 to 10 carbon atoms to give a compound (1).

15. A process for preparing a pyrrolidinone derivative of structure (1)

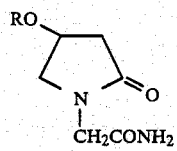
(1)

in which R is straight or branched alkyl of 1 to 4 carbon atoms, comprising:
(a) reacting an alkyl 3,4-epoxybutanoate of structure (4)

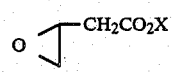
(4)

wherein X is alkyl of 1 to 10 carbon atoms with a glycinamide derivative of structure (5)

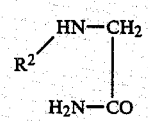
(5)

wherein $R^2$ is benzyl, α-methylbenzyl or p-methoxybenzyl to give a compound of structure (2)

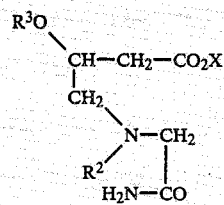
(2)

wherein X and $R_2$ are as defined above, and $R^3$ is hydrogen;
(b) N-deprotecting the compound of structure (2) to give a compound of structure (3)

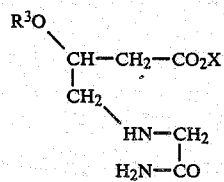
(3)

wherein X and $R^3$ are as defined above;
(c) cyclizing the compound of structure (3) intramolecularly by heating at 0° to 120° C.; and
(d) reacting the cyclized compound with an alkyl halide or sulfate in which alkyl is of 1 to 4 carbon atoms to give a compound (1).

16. A process for preparing a pyrrolidinone derivative of structure (1)

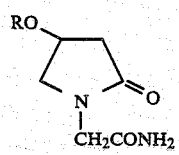
(1)

in which R is straight or branched alkyl of 1 to 4 carbon atoms, comprising:
(a) reacting an alkyl 3,4-epoxybutanoate of structure (4)

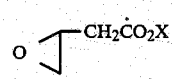
(4)

wherein X is alkyl of 1 to 10 carbon atoms with a glycinamide derivative of structure (5)

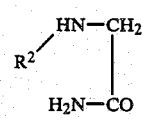
(5)

wherein $R^2$ is benzyl, α-methylbenzyl or p-methoxybenzyl to give a compound a structure (2)

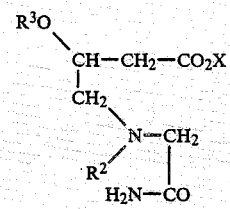
(2)

wherein X and $R_2$ are as defined above, and $R^3$ is hydrogen;
(b) reacting said compound of structure (2) with an alkyl halide or sulfate to yield a compound of structure (2) in which $R^3$ is straight or branched alkyl of 1 to 4 carbon atoms;
(c) N-deprotecting said compound of structure (2) to give a compound of structure (3)

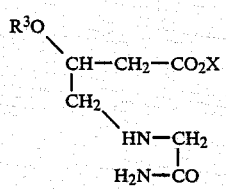
(3)

wherein X and $R^3$ are as defined above; and
(d) cyclizing the compound of structure (3) intermolecularly by heating at 0° to 120° C.

17. The process of claim 13, 14, 15, or 16 wherein the compound of structure (2) is N-deprotected by catalytic hydrogenation.

18. The process of claim 13, 14, 15, or 16 wherein the compound of structure (2) is N-deprotected by treatment with a mixture of formic acid and methanol and palladium-on-charcoal.

19. A process for preparing a pyrrolidinone derivative of structure (1)

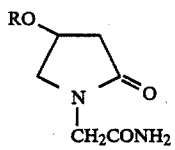

in which R is hydrogen, comprising
(a) reacting an alkyl 3,4-epoxybutanoate of structure (4)

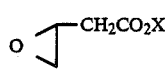

wherein X is alkyl of 1 to 10 carbon atoms with a glycinamide derivative of structure (5A)

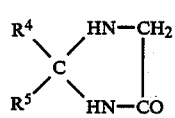

wherein $R^4$ and $R^5$ are independently hydrogen, alkyl containing 1 to 4 carbon atoms, phenyl, or $R^4$ and $R^5$ together are 1,4-butylene or 1,5-pentylene, to give a compound of structure (2A)

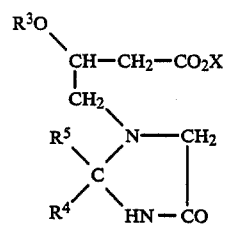

wherein $R^4$, $R^5$ and X are as defined above, and $R^3$ is R as defined above; and
(b) deprotecting and cyclizing intermolecularly by heating in 90° to 160° C. the compound of structure (2A).

20. A process for preparing a pyrrolidinone derivative of structure (1)

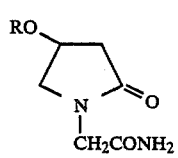

in which R is alkanoyl containing 1 to 10 carbon atoms, comprising:
(a) reacting an alkyl 3,4-epoxybutanoate of structure (4)

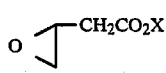

wherein X is alkyl of 1 to 10 carbon atoms with a glycinamide derivative of structure (5A)

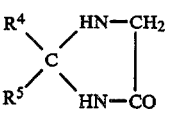

wherein $R^4$ and $R^5$ are independently hydrogen, alkyl containing 1 to 4 carbon atoms, phenyl, or $R^4$ and $R^5$ together are 1,4-butylene or 1,5-pentylene, to give a compound of structure (2A)

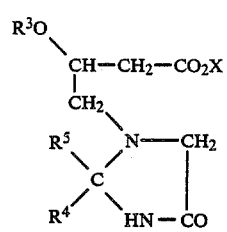

wherein $R^4$, $R^5$ and X are as defined above, and $R^3$ is hydrogen;
(b) N-deprotecting and cyclizing intermolecularly by heating at 90° to 160° C. the compound of structure (2A); and
(c) reacting the cyclized compound with an acyl halide or acid anhydride in which acyl is alkanoyl containing 1 to 10 carbon atoms to give a compound (1).

21. A process for preparing a pyrrolidinone derivative of structure (1)

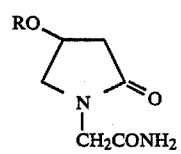

in which R is straight or branched alkyl of 1 to 4 carbon atoms comprising:
(a) reacting an alkyl 3,4-epoxybutanoate of structure (4)

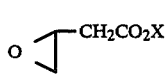

wherein X is alkyl of 1 to 10 carbon atoms with a glycinamide derivative of structure (5A)

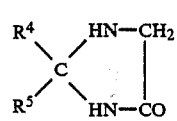

wherein $R^4$ and $R^5$ are independently hydrogen, alkyl containing 1 to 4 carbon atoms, phenyl, or $R^4$ and $R^5$ together are 1,4-butylene or 1,5-pentylene, to give a compound of structure (2A)

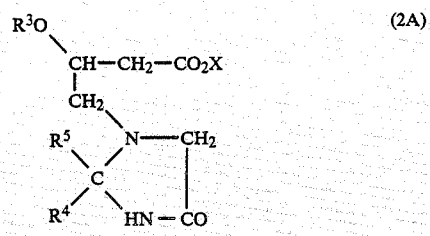 (2A)

wherein $R^4$, $R^5$ and X are as defined above, and $R^3$ is hydrogen;

(b) N-deprotecting and cyclizing intermolecularly by heating at 90° to 160° C. the compound of structure (2A); and (c) reacting the cyclized compound with an alkyl halide or sulfate in which alkyl is of 1 to 4 carbon atoms to give a compound (1).

22. A process for preparing a pyrrolidinone derivative of structure (1)

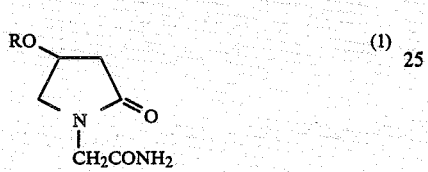 (1)

in which is straight or branched alkyl of 1 to 4 carbon atoms comprising:

(a) reacting an alkyl 3,4-epoxybutanoate of structure (4)

 (4)

wherein X is alkyl of 1 to 10 carbon atoms with a glycinamide derivative of structure (5A)

 (5A)

wherein $R^4$ and $R^5$ are independently hydrogen, alkyl containing 1 to 4 carbon atoms, phenyl, or $R^4$ and $R^5$ together are 1,4-butylene or 1,5-pentylene, to give a compound of structure (2A)

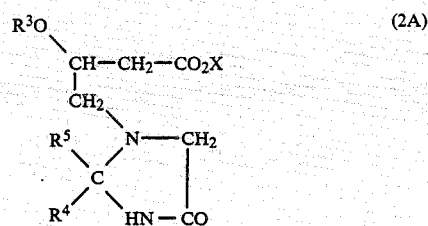 (2A)

wherein $R^4$, $R^5$ and X are as defined above, and $R^3$ is hydrogen;

(b) reacting said compound of structure (2A) with an alkyl halide or sulfate to yield a compound of structure (2A) in which $R^3$ is a straight or branched alkyl of 1 to 4 carbon atoms;

(c) N-deprotecting and cyclizing intermolecularly by heating at 90° to 160° C. the compound of structure (2A).

23. The process of claim 19, 20, 21 or 22 in which N-deprotection is effected in the presence of acetic or benzoic acid.

24. The process of claim 19, 20, 21 or 22 in which in the compound of structure (2A) $R^4$ is hydrogen, $R^5$ is an isopropyl group and $R^3$ is hydrogen.

* * * * *